United States Patent
Kawanishi et al.

(10) Patent No.: US 6,850,797 B2
(45) Date of Patent: Feb. 1, 2005

(54) VISCERAL FAT METER

(75) Inventors: Shozo Kawanishi, Akashi (JP); Koichi Okita, Akashi (JP)

(73) Assignee: Yamoto Scale Company, Akashi (JP)

( * ) Notice: Subject to any disclaimer, the term of this patent is extended or adjusted under 35 U.S.C. 154(b) by 0 days.

(21) Appl. No.: 10/048,801

(22) PCT Filed: May 28, 2001

(86) PCT No.: PCT/JP01/04440

§ 371 (c)(1),
(2), (4) Date: May 1, 2002

(87) PCT Pub. No.: WO01/91638

PCT Pub. Date: Dec. 6, 2001

(65) Prior Publication Data

US 2002/0151815 A1 Oct. 17, 2002

(30) Foreign Application Priority Data

May 31, 2000 (JP) .................................. 2000-162338

(51) Int. Cl.⁷ .............................................. A61B 5/05
(52) U.S. Cl. ...................................................... 600/547
(58) Field of Search ................................ 600/547, 587, 600/595

(56) References Cited

U.S. PATENT DOCUMENTS

| 5,579,782 | A | 12/1996 | Masuo |
| 6,369,337 | B1 | 4/2002 | Machiyama et al. |
| 6,487,445 | B1 * | 11/2002 | Serita et al. ................. 600/547 |

FOREIGN PATENT DOCUMENTS

| EP | 1 063 500 A2 | 12/2000 |
| EP | 1 063 500 A3 | 4/2001 |
| GB | 2176323 | 12/1986 |
| JP | 11-244252 | 9/1999 |

* cited by examiner

Primary Examiner—MaryBeth Jones
Assistant Examiner—Brian Szmal
(74) Attorney, Agent, or Firm—Kolisch Hartwell, P.C.

(57) ABSTRACT

A visceral fat determining device which is easy to operate at home and capable of providing information associated with visceral fat of a subject is disclosed. The visceral fat determining device is comprising means for inputting personal data representing vital characteristics of the subject, a data processing unit that can process various types of calculations, and a display portion capable of displaying the personal data and the calculation results. Quantitative information on the visceral fat of the subject can be obtained through the calculation based on the abdominal girth of the subject, which is a circumferential length of a torso of the subject.

27 Claims, 6 Drawing Sheets

VISCERAL FAT METER

TECHNICAL FIELD

The present invention relates to a visceral fat determining device capable of obtaining information on visceral fat that is part of internal body fat of a human body through a simple operation.

BACKGROUND ART

Conventionally, attention has been paid to internal body fat content of a person in view of health maintenance. In other words, since a rise in internal body fat content of a person may increase a risk for the person to get so called adult diseases, monitoring the internal body fat content of the person may prevent the adult diseases. BMI has been widely used as an index to evaluate the internal body fat content since it can be easily calculated from height and weight of an individual person.

Another useful index to evaluate the internal body fat content of a person is a body fat ratio. Recently, various types of body fat meters capable of measuring the body fat ratio are available on the market, and, with these body fat meters, the body fat ratio can be easily measured at home.

Among the internal body fat, the visceral fat has been believed to be a factor particularly contributing to various complications of arteriosclerosis, diabetes, and etc. For this reason, the visceral fat content has been becoming an important factor in view of health maintenance.

The BMI and the body fat ratio described above are information obtained as average data on internal body fat content in the whole body. Hence, even if the result of the BMI or the body fat ratio does not indicate any health problem, it does not necessarily mean that there is no health problem in relation with the visceral fat content.

Information on the visceral fat can be obtained through a diagnosing method such as abdominal tomography by means of CT scanning, MRI, and etc. This method allows directly observing the abdominal portion itself, thereby making it possible to accurately obtain information on the visceral fat.

Such a method, however, is problematic in that the procedure requires a large scale apparatus installed in a major hospital, a certain length of time necessary for measurement and data analysis, and highly specific technical knowledge for the operation and data analysis. Hence, the method is not suitable for use at home to obtain the visceral fat content.

It is, therefore, the object of the present invention to provide a visceral fat determining device that can be easily used at home or the like for obtaining information on the visceral fat.

DISCLOSURE OF THE INVENTION

In order to achieve the object, according to the present invention, a visceral fat determining device comprises:

input means for inputting personal data including an abdominal girth $W_L$ which is a circumferential length of a torso of a subject;

a data processing unit that stores the personal data and calculates quantitative information on abdominal visceral fat of the subject based on the personal data; and a display portion that displays the personal data and a result of the calculation performed by the data processing unit, wherein the quantitative information on abdominal visceral fat of the subject is calculated based on the abdominal girth of the subject.

The state of abdominal visceral fat of the subject has been believed to be strongly correlated with the abdominal girth $W_L$ that is one of physical characteristics of the subject. In the visceral fat determining devise of the present invention, the quantitative information on abdominal visceral fat of the subject can be obtained based on the abdominal girth $W_L$ of the subject. Therefore, according to the present invention, information on the abdominal visceral fat which is strongly related to the health condition of the subject can be easily obtained at home or the like.

In the visceral fat determining device of the present invention, the quantitative information on the abdominal visceral fat may be an amount of the abdominal visceral fat obtained based on the abdominal girth $W_L$ of the subject. The amount of abdominal visceral fat of the subject is information deeply related to the health condition of the subject and therefore can be monitored to foresee a possibility of being suffered from the adult diseases.

According to the present invention, the visceral fat determining device further comprises:

body fat ratio measuring means for measuring a bioelectrical impedance Z of the subject through electrodes in contact with the end portions of the subject and for calculating a body fat ratio FAT of the subject based on the measured bioelectrical impedance and the inputted personal data or part of the data, wherein the body fat ratio FAT obtained by the body fat ratio measuring means can be displayed on the display portion.

With this configuration, the visceral fat determining device of the present invention is not only capable of obtaining information on the abdominal visceral fat but also capable of obtaining the body fat ratio FAT.

Furthermore, according to the present invention, the visceral fat determining device can be configured to calculate an estimated value of an abdominal visceral fat cross sectional area VA as information associated with the visceral fat. When obtaining the estimated value of an abdominal visceral fat cross sectional area VA, a specific correlation between the abdominal girth $W_L$ and the abdominal visceral fat cross sectional area VA is determined based on statistical analysis of correlation between actual values of an abdominal visceral fat cross sectional area VA and the personal data including the abdominal girth $W_L$ of a number of human samples randomly selected. Then, the estimated value of an abdominal visceral fat cross sectional area VA of an individual subject can be accurately calculated based on the abdominal girth $W_L$ and other data of the individual subject to by applying the determined correlation to the individual subject.

A visceral fat determining device capable of obtaining such an estimated value of an abdominal visceral fat cross sectional area VA may comprise:

input means for inputting personal data including an abdominal girth $W_L$ which is a circumferential length of a torso of a subject;

a data processing unit that stores the personal data and calculates an estimated value of an abdominal visceral fat cross sectional area VA of the subject based on the personal data; and a display portion that displays the personal data and a result of the calculation performed by the data processing unit, wherein the data processing unit stores a first regression coefficient of the abdominal girth $W_L$ and a first regression constant which are obtained based on statistical analysis of correlation between actually measured values of the abdominal visceral fat cross sectional area VA obtained in abdominal tomography of human bodies of random samples and values of the abdominal girth $W_L$ of the human samples, and the estimated value of an abdominal visceral fat cross sectional area VA of the subject is obtained based on a value of the abdominal girth $W_L$ of the subject, the first regression coefficient of the abdominal girth $W_L$, and the first regression constant.

The present invention of the visceral fat determining device is based on the fact that the abdominal visceral fat cross sectional area VA is deeply correlated with the abdominal girth $W_L$. The data processing unit stores a first regression coefficient of the abdominal girth $W_L$ and a first regression constant obtained based on statistical analysis of correlation between actually measured values of the abdominal visceral fat cross sectional area VA obtained in abdominal tomography of human bodies of random samples and values of the abdominal girths $W_L$ of the human samples. When a value of the abdominal girth $W_L$ of the subject is inputted, an estimated value of the abdominal visceral fat cross sectional area VA is calculated based on the first regression coefficient of the abdominal girth $W_L$ and the first regression constant.

As described above, according to the visceral fat determining device of the present invention, the estimated value of an abdominal visceral fat cross sectional area VA of a subject can be obtained as the information associated with the visceral fat of the subject by simply inputting a value of the abdominal girth $W_L$ which is part of the personal data. In this way, the estimated value of an abdominal visceral fat cross sectional area VA that is information deeply related to the health condition can be easily obtained.

Furthermore, a visceral fat determining device capable of calculating the abdominal visceral fat cross section area VA may comprise:

input means for inputting personal data including an abdominal girth $W_L$ that is a circumferential length of a torso of a subject, height, and weight of the subject;

a data processing unit that stores the personal data and calculates an estimated value of an abdominal visceral fat cross sectional area VA of the subject based on the personal data; and a display portion that displays the personal data and the a result of the calculation performed by the data processing unit, wherein the data processing unit stores a second regression coefficient of the abdominal girth $W_L$, a first regression coefficient of the BMI, and a second regression constant which are obtained based on statistical analysis of the correlation between actually measured values of the abdominal visceral fat cross sectional area VA obtained in abdominal tomography of human bodies of random samples and values of the abdominal girth $W_L$ and values of the BMI of the human samples related to the level of the obesity, and the data processing unit calculates the estimated value of an abdominal visceral fat cross sectional area VA of the subject based on a value of the abdominal girth $W_L$, a value of the BMI, the second regression coefficient of the abdominal girth $W_L$, the first regression coefficient of the BMI, and the second regression constant.

The present invention of the visceral fat determining device is based on the fact that the abdominal visceral fat cross sectional area VA is correlated with the BMI in addition to the abdominal girth $W_L$. The data processing unit stores a second regression coefficient of the abdominal girth $W_L$ and a first regression coefficient of the BMI, and a second regression constant which are obtained based on statistical analysis of correlation between actually measured values of the abdominal visceral fat cross sectional area VA obtained in abdominal tomography of human bodies of random samples and values of the abdominal girth $W_L$ and values of the BMI of the human samples. Then, with the visceral fat determining device of the present invention, when a value of the abdominal girth $W_L$ and a value of the BMI of a subject are inputted, an estimated value of the abdominal visceral fat cross sectional area VA of the subject is calculated. Therefore, in the visceral fat determining device of the present invention, in addition to the abdominal girth $W_L$, the BMI of the subject can be well reflected in obtaining the abdominal visceral fat cross sectional area VA.

Furthermore, according to the present invention, a visceral fat determining device may comprise:

input means for inputting personal data including an abdominal girth $W_L$ that is a circumferential length of a torso of a subject, height, weight, sex, and age of the subject;

a data processing unit that stores the personal data and calculates an estimated value of an abdominal visceral fat cross sectional area VA of the subject based on the personal data;

a display portion that displays the personal data and a result of the calculation performed by the data processing unit; and body fat ratio measuring means for measuring a bioelectrical impedance Z of the subject through electrodes in contact with end portions of the subject's body and for obtaining a body fat ratio FAT of the subject based on the measured bioelectrical impedance Z and the inputted personal data or part of the data, wherein the data processing unit stores a third regression coefficient of an abdominal girth $W_L$, a first regression coefficient of body fat ratio FAT, and a third regression constant which are obtained based on statistical analysis of the correlation between actually measured values of the abdominal visceral fat cross sectional area VA obtained in abdominal tomography of human bodies of random samples and values of the abdominal girth $W_L$ and values of the body fat ratio FAT of the human samples, and the data processing unit calculates the estimated value of an abdominal visceral fat cross sectional area VA of the subject based on a value of the abdominal girth $W_L$, a value of the body fat ratio FAT obtained by the body fat ratio measuring means, the third regression coefficient of the abdominal girth $W_L$, and the first regression coefficient of the body fat ratio FAT, and the third regression constant.

The invention of the visceral fat determining device is based on the fact that the abdominal visceral fat cross sectional area VA is correlated with the body fat ratio FAT in addition to the abdominal girth $W_L$. The data processing unit stores a third regression coefficient of the abdominal girth $W_L$ and a first regression coefficient of the body fat ratio FAT, and a third regression constant which are obtained based on statistical analysis of the correlation between actually measured values of the abdominal visceral fat cross sectional area VA obtained in abdominal tomography of human bodies of random samples and values of the abdominal girth $W_L$ and values of the body fat ratio FAT. According to the visceral fat determining device, when a value of the abdominal girth $W_L$ and a value of the body fat ratio FAT of the subject are inputted, an estimated value of the abdominal visceral fat cross sectional area VA of the subject is calculated. Therefore, according to the visceral fat determining device of the present invention, the body fat ratio FAT of the subject can be well reflected in obtaining the abdominal visceral fat cross sectional area VA in addition to the abdominal girth $W_L$.

Furthermore, a visceral fat determining device of the present invention may comprise:

input means for inputting personal data including an abdominal girth $W_L$ that is a circumferential length of a torso of a subject, height, weight, and a thickness of an abdominal subcutaneous fat s of the subject;

a data processing unit that stores the personal data and calculates an estimated value of an abdominal visceral fat cross sectional area VA of the subject based on the personal data; and a display portion that displays the personal data and a result of the calculation performed by the data processing unit, wherein the data processing unit stores a fourth regression coefficient of the abdominal girth $W_L$, a second regression coefficient of BMI, and a first regression coefficient of the thickness of the abdominal subcutaneous fat s, and a fourth regression constant which are obtained based on statistical analysis of correlation between actually measured values of the abdominal visceral fat cross sectional area VA obtained in abdominal tomography of human bodies of random samples and values of the BMI which is related to the obesity level of the human samples and values of the thickness of the abdominal subcutaneous fat s of the human samples, and the data processing unit calculates the estimated value of an abdominal visceral fat cross sectional area VA of the subject based on a value of the abdominal girth $W_L$, a value of the BMI, a value of the thickness of abdominal subcutaneous fat s, the fourth regression coefficient of the abdominal girth $W_L$, the second regression coefficient of the BMI, the first regression coefficient of the thickness of abdominal subcutaneous fat s, and the fourth regression constant.

The present invention of the visceral fat determining device is based on the fact that the abdominal visceral fat cross sectional area VA is correlated with the BMI, the thickness of the abdominal subcutaneous fat s in addition to the abdominal girth $W_L$. The visceral fat determining device of the present invention stores a fourth regression coefficient of the abdominal girth $W_L$, a second regression coefficient of the BMI, and a first regression coefficient of the thickness of abdominal subcutaneous fat s, and a fourth regression constant obtained based on statistical analysis of correlation between actually measured values of the abdominal visceral fat cross sectional areas VA obtained in abdominal tomography of human bodies of random samples and values of the abdominal girth $W_L$, values of the BMI, and values of the thickness of abdominal subcutaneous fat s of the human samples. According to the visceral fat determining device, when a value of the abdominal girth $W_L$, a value of the BMI, and a value of the thickness of abdominal subcutaneous fat s of the subject are inputted, an estimated value of the abdominal visceral fat cross sectional area VA of the subject is calculated. Therefore, in the visceral fat determining device of the present invention, in addition to the abdominal girth $W_L$, the BMI and the thickness of abdominal subcutaneous fat s can be well reflected in obtaining the abdominal visceral fat cross sectional area VA.

Furthermore, a visceral fat determining device of the present invention may comprise:

input means for inputting personal data including an abdominal girth $W_L$ that is a circumferential length of a torso of a subject, height, weight, sex, age, and a thickness of abdominal subcutaneous fat s of the subject;

a data processing unit that stores the personal data and calculates an estimated value of an abdominal visceral fat cross sectional area VA of the subject based on the personal data;

a display portion that displays the personal data and a result of the calculation performed by the data processing unit; and body fat ratio measuring means for measuring a bioelectrical impedance Z of the subject through electrodes in contact with end portions of the subject's body and for obtaining a body fat ratio FAT of the subject based on the measured bioelectrical impedance Z and the inputted personal data or part of the data, wherein the data processing unit stores a fifth regression coefficient of the abdominal girth $W_L$, a second regression coefficient of the body fat ratio FAT, a second regression coefficient of the thickness of the abdominal subcutaneous fat s and a fifth regression constant obtained based on statistical analysis of correlation between actually measured values of the abdominal visceral fat cross sectional area VA obtained in abdominal tomography of human bodies of random samples and values of the abdominal girth $W_L$ of the human samples, values of the body fat ratio FAT of the human samples, and values of the thickness of abdominal subcutaneous fat s, wherein the data processing unit calculates the estimated value of an abdominal visceral fat cross sectional area VA of the subject based on a value of the abdominal girth $W_L$, a value of the body fat ratio FAT obtained with the body fat ratio measuring means, a value of the thickness of abdominal subcutaneous fat s, the fifth regression coefficient of the abdominal girth $W_L$, the second regression coefficient of the body fat ratio FAT, the second regression coefficient of the thickness of abdominal subcutaneous fat s, and the fifth regression constant.

The present invention of the visceral fat determining device is based on the fact that the abdominal visceral fat cross sectional area VA is correlated with the body fat ratio FAT and the thickness of the abdominal subcutaneous fat s in addition to the abdominal girth $W_L$. The visceral fat determining device of the present invention stores a fifth regression coefficient of the abdominal girth $W_L$, a second regression coefficient of the body fat ratio FAT, a second regression coefficient of the thickness of abdominal subcutaneous fat s, and a fifth regression constant obtained based on statistical analysis of correlation between actually measured values of the abdominal visceral fat cross sectional area VA obtained in abdominal tomography of human bodies of random samples and values of the abdominal girth $W_L$, values of the body fat ratio FAT, and values of the thickness of abdominal subcutaneous fat s. With this configuration, when a value of the abdominal girth $W_L$, a value of the body fat ratio FAT, and a value of the thickness of abdominal subcutaneous fat s of the subject are inputted, an estimated value of the abdominal visceral fat cross sectional area VA of the subject is calculated. Therefore, in the visceral fat determining device of the present invention, in addition to the abdominal girth $W_L$, the body fat ratio FAT and the thickness of the abdominal subcutaneous fat s are well reflected in obtaining the estimated value of the abdominal visceral fat cross sectional area VA. Also, the visceral fat determining device of the present invention in which the thickness of the abdominal subcutaneous fat s is inputted can be configured to further obtain an abdominal subcutaneous fat cross sectional area SA based on the thickness of the abdominal subcutaneous fat s and the abdominal girth $W_L$ of the subject.

Furthermore, the visceral fat determining device of the present invention can be configured to further calculate a ratio of the estimated value of an abdominal visceral fat cross sectional area VA to the abdominal subcutaneous fat cross sectional area SA, VSR. Even furthermore, the visceral fat determining device of the present invention can be configured to further calculate a total abdominal fat cross sectional area WA based on the estimated value of an abdominal visceral fat cross sectional area VA and the abdominal subcutaneous fat cross sectional area SA of the subject. The abdominal subcutaneous fat cross sectional area SA obtained with the visceral fat determining device of the present invention offers the following important advantages.

It is recently reported that a hormone secreted from subcutaneous fat of a person tends to reduce internal body fat of the person. Furthermore, the subcutaneous fat tends to reduce the negative influence of the visceral fat accumulated in the body due to the intake of excess nutrition. Therefore, information on the abdominal subcutaneous fat or the ratio of the subcutaneous fat to the visceral fat can be used as an important index for assessing the health condition.

Furthermore, a visceral fat determining device of the present invention may comprise:

input means for inputting personal data including an abdominal girth $W_L$ that is a circumferential length of a torso of a subject and height of the subject;

a data processing unit that stores the personal data and calculates an estimated value of an abdominal visceral fat cross sectional area VA of the subject based on the personal data; and a display portion that displays the personal data and a result of the calculation performed by the data processing unit, wherein the data processing unit stores a first regression coefficient of an abdominal girth index and a sixth regression constant obtained based on statistical analysis of correlation between actually measured values of the abdominal visceral fat cross sectional area VA obtained in abdominal tomography of human bodies of random samples and values of the abdominal girth index of the human samples obtained based on the abdominal girth $W_L$ and the height of the human samples, and wherein the data processing unit calculates the estimated value of an abdominal visceral fat cross sectional area VA of the subject based on a value of the abdominal girth index, the first regression coefficient of the abdominal girth index, and the sixth regression constant.

In the visceral fat determining device of the present invention, an estimated value of an abdominal visceral fat cross sectional area VA of a subject is calculated based on the correlation with the abdominal girth index. Herein, an abdominal girth index is defined as an index obtained by dividing a square of the abdominal girth $W_L^2$ with height of the subject. This index is deeply correlated with the obesity.

A visceral fat determining device of the present invention may comprise:

input means for inputting personal data including an abdominal girth $W_L$ that is a circumferential length of a torso of a subject and height of the subject;

a data processing unit that stores the personal data and calculates an estimated value of an abdominal visceral fat cross sectional area VA of the subject based on the personal data;

a display portion that displays the personal data and a result of the calculation performed by the data processing unit; and impedance measuring means for measuring a bioelectrical impedance Z of the subject through electrodes in contact with end portions of the subject's body, wherein the data processing unit stores an eighth regression coefficient of an abdominal girth $W_L$ and a first regression coefficient of a term $(T_L^2/Z)$, and an eleventh regression constant which are obtained based on statistical analysis of correlation between the actually measured values of the abdominal visceral fat cross sectional area VA obtained in abdominal tomography of human bodies of random samples and values of the abdominal girth $W_L$ of the human samples and values of the term $(T_L^2/Z)$ obtained by dividing a square of height $T_L^2$ by the bioelectrical impedance Z, and wherein the data processing unit calculates the estimated value of an abdominal visceral fat cross sectional area VA of the subject based on a value of the abdominal girth $W_L$, a value of the bioelectrical impedance Z measured with the impedance measuring means, a value of the height $T_L$ obtained through the input means, the eighth regression coefficient of the abdominal girth $W_L$, and the first regression coefficient of the term $(T_L^2/Z)$ and the eleventh regression constant.

The present invention of the visceral fat determining device is based on the fact that the abdominal visceral fat cross sectional area VA is correlated with the term $(T_L^2/Z)$ in addition to the abdominal girth $W_L$. The visceral fat determining device of the present invention stores an eighth regression coefficient of the abdominal girth $W_L$, and a first regression coefficient of the term $(T_L^2/Z)$, and an eleventh regression constant obtained based on statistical analysis of correlation between actually measured values of the abdominal visceral fat cross sectional areas VA obtained in abdominal tomography of human bodies of random samples and values of the abdominal girth $W_L$ and values of the term $(T_L^2/Z)$. With this configuration, when a value of the abdominal girth $W_L$ and a value of the height $T_L$ of a subject are inputted together with a value of the measured bioelectrical impedance Z, an estimated value of the abdominal visceral fat cross sectional area VA of the subject is calculated. Therefore, in the visceral fat determining device of the present invention, in addition to the abdominal girth $W_L$, the term $(T_L^2/Z)$ can be reflected in obtaining the estimated value of the abdominal visceral fat cross sectional area VA.

Furthermore, a visceral fat determining device of the present invention may comprise:

input means for inputting personal data including an abdominal girth $W_L$ that is a circumferential length of a torso of a subject and height of the subject;

a data processing unit that stores the personal data and calculates an estimated value of an abdominal visceral fat cross sectional area VA of the subject based on the personal data;

a display portion that displays the personal data and a result of the calculation performed by the data processing unit; and impedance measuring means for measuring a bioelectrical impedance Z of a subject through electrodes in contact with end portions of the subject's body, wherein the data processing unit stores a ninth regression coefficient of the abdominal girth $W_L$, a first regression coefficient of the bioelectrical impedance Z, and a twelfth regression constant obtained based on statistical analysis of correlation between actually measured values of the abdominal visceral fat cross sectional area VA obtained in abdominal tomography of human bodies of random samples and values of the abdominal girth $W_L$ of the human samples and values of the bioelectrical Z of the human samples, wherein the data processing unit calculates the estimated value of an abdominal visceral fat cross sectional area VA of the subject based on a value of the abdominal girth $W_L$, a value of the bioelectrical impedance Z measured with the impedance measuring means, the ninth regression coefficient of the abdominal girth $W_L$, and the first regression coefficient of the bioelectrical impedance Z, and the twelfth regression constant.

The present invention of the visceral fat determining device is based on the fact that the abdominal visceral fat cross sectional area VA is correlated with the bioelectrical impedance Z in addition to the abdominal girth $W_L$. The visceral fat determining device of the present invention stores a ninth regression coefficient of the abdominal girth $W_L$ and a first regression coefficient of the bioelectrical impedance Z, and a twelfth regression constant obtained based on statistical analysis of correlation between actually measured values of an abdominal visceral fat cross sectional area VA obtained in abdominal tomography of human bodies of random samples and values of the abdominal girth $W_L$ of the human samples and values of the bioelectrical impedance Z of the human samples. With this configuration, when a value of the abdominal girth $W_L$ of a subject is inputted together with a value of the bioelectrical impedance Z measured, an estimated value of the abdominal visceral fat cross sectional area VA of the subject is calculated. Therefore, in the visceral fat determining device of the present invention, in addition to the abdominal girth $W_L$, the bioelectrical impedance Z can be reflected in obtaining the estimated value of the abdominal visceral fat cross sectional area VA.

Furthermore, a visceral fat determining device of the present invention may comprise:

input means for inputting personal data including an abdominal girth $W_L$ that is a circumferential length of a torso of a subject, height, weight, sex, and age of the subject;

a data processing unit that stores the personal data and calculates an estimated value of an abdominal visceral fat cross sectional area VA of the subject based on the personal data;

a display portion that displays the personal data and a result of the calculation performed by the data processing unit; and body fat ratio measuring means for measuring a bioelectrical impedance Z of a subject through electrodes in contact with end portions of the subject's body and for obtaining a body fat ratio FAT of the subject based on the measured bioelectrical impedance Z and the inputted personal data or part of the data, wherein the data processing unit stores a first regression coefficient of a term ($W_L^2 \cdot T_L \cdot$age) and a first regression coefficient of a term ($W_L^2 \cdot T_L \cdot$FAT), and a thirteenth regression constant obtained based on statistical analysis of correlation between actually measured values of the abdominal visceral fat cross sectional area VA obtained in abdominal tomography of human bodies of random samples and values of the term ($W_L^2 \cdot T_L \cdot$age) obtained by multiplying a square of an abdominal girth of the human samples $W_L^2$, the height $T_L$ of the human samples, and the age of the human samples and values of the term of ($W_L^2 \cdot T_L \cdot$FAT) obtained by multiplying a square of an abdominal girth of the human samples $W_L^2$, the height $T_L$ of the human samples, and a body fat ratio FAT of the human samples, and when inputted subject's personal data of sex is "male", the data processing unit calculates the estimated value of an abdominal visceral fat cross sectional area VA of the male subject based on a value of the abdominal girth $W_L$ of the male subject, a value of the age of the male subject inputted through the input means, a value of the body fat ratio FAT of the male subject measured with the body fat ratio measuring means, the first regression coefficient of the term ($W_L^2 \cdot T_L \cdot$age), and the first regression coefficient of the term ($W_L^2 \cdot T_L \cdot$FAT) and the thirteenth regression constant.

In the case that the subject is male, the present invention of the visceral fat determining device is based on the fact that the abdominal visceral fat cross sectional area VA is deeply correlated with the terms ($W_L^2 \cdot T_L \cdot$age) and ($W_L^2 \cdot T_L \cdot$FAT). Therefore, the visceral fat determining device of the present invention stores a first regression coefficient of the term ($W_L^2 \cdot T_L \cdot$age) and a first regression coefficient of the term ($W_L^2 \cdot T_L \cdot$FAT) and a thirteenth regression constant obtained based on statistical analysis of correlation between actually measured values of the abdominal visceral fat cross sectional area VA obtained in abdominal tomography of human bodies of random male samples and values of the term ($W_L^2 \cdot T_L \cdot$age) of the human male samples and values of the term ($W_L^2 \cdot T_L \cdot$FAT) of the human male samples. When a value of the abdominal girth $W_L$ of the male subject and a value of the height $T_L$ of the male subject are inputted together with a measured value of the body fat ratio FAT of the male subject, an estimated value of the abdominal visceral fat cross sectional area VA of the male subject is calculated. In this way, according to the visceral fat determining device of the present invention, when the subject is male, an estimated value of the abdominal visceral fat cross sectional area VA of the male subject is more accurately calculated.

Furthermore, a visceral fat determining device of the present invention may comprise:

input means for inputting personal data including an abdominal girth $W_L$ that is a circumferential length of a torso of a subject, height, weight, sex, and age of the subject;

a data processing unit that stores the personal data and calculates an estimated value of an abdominal visceral fat cross sectional area VA of the subject based on the personal data;

a display portion that displays the personal data and a result of the calculation performed by the data processing unit; and body fat ratio measuring means for measuring a bioelectrical impedance Z of a subject through electrodes in contact with end portions of the subject's body and for obtaining a body fat ratio FAT of the subject based on the measured bioelectrical impedance Z and the inputted personal data or part of the data, wherein the data processing unit stores a second regression coefficient of the term ($W_L^2 \cdot T_L \cdot$age) and a fifth regression coefficient of the body fat ratio FAT, and a fourteenth regression constant obtained based on statistical analysis of correlation between actually measured values of the abdominal visceral fat cross sectional area VA obtained in abdominal tomography of human bodies of random samples and values of the term ($W_L^2 \cdot T_L \cdot$age) obtained by multiplying a square of an abdominal girth of the human samples $W_L^2$, the height $T_L$ of the human samples, and the age of the human samples and values of the body fat ratio FAT of the human samples, and when inputted subject's personal data of sex is "female", the data processing unit calculates the estimated value of an abdominal visceral fat cross sectional area VA of the female subject based on a value of the abdominal girth $W_L$ of the female subject, a value of the age of the female subject inputted through the input means, a value of the body fat ratio FAT of the female subject measured with the body fat ratio measuring means, the second regression coefficient of the term ($W_L^2 \cdot T_L \cdot$age), the fifth regression coefficient of the body fat ratio FAT, and the fourteenth regression constant.

The present invention of the visceral fat determining device is based on the fact that the abdominal visceral fat cross sectional area VA is deeply correlated with the term ($W_L^2 \cdot T_L \cdot$age) and the body fat ratio FAT of the female subject. The visceral fat determining device of the present invention stores a second regression coefficient of the term ($W_L^2 \cdot T_L \cdot$age) and a fifth regression coefficient of the body fat ratio FAT, and a fourteenth regression constant obtained based on statistical analysis of correlation between actually measured values of the abdominal visceral fat cross sectional area VA obtained in abdominal tomography of human bodies of random female samples and values of the term ($W_L^2 \cdot T_L \cdot$age) of the human female samples and values of the body fat ratio FAT of the human female samples.

When a value of the abdominal girth $W_L$ of the female subject, a value of the height $T_L$ of the female subject, a value of the age of the female subject are inputted together with a measured value of the body fat ratio FAT, an estimated value of the abdominal visceral fat cross sectional area VA of the female subject is calculated. In this way, according to the visceral fat determining device of the present invention, when the subject is female as described above, an estimated value of the abdominal visceral fat cross sectional area VA of the female subject is more accurately calculated.

Furthermore, the visceral fat determining device of the present invention can be configured in such a way that the calculation of the estimated value of an abdominal visceral fat cross sectional area VA of a subject may be performed with addition of a correction term of the age and a correction term of the sex of the subject. In this configuration, the information associated with the physical characteristics of the subject such as age and sex can be well reflected in obtaining the estimated value of the abdominal visceral fat cross sectional area VA of the subject. An estimated value of an abdominal visceral fat cross sectional area VA of a subject can be corrected with the age, the sex, or both.

Furthermore, the visceral fat determining device of the present invention capable of calculating an abdominal visceral fat cross sectional area VA of a subject can be configured to include body fat ratio measuring means for measuring a body fat ratio FAT of the subject and a display portion that displays the body fat ratio FAT of the subject even if the above visceral fat determining device does not calculate the abdominal visceral fat cross sectional area VA of the subject through the measurement of the body fat ratio FAT. In this configuration, in addition to the abdominal visceral fat cross sectional area VA of the subject, the body fat ratio FAT can also be monitored through the display.

Furthermore, the visceral fat determining device of the present invention can be configured to display on the display portion an estimated value of an abdominal visceral fat cross sectional area VA of a subject in accordance with a plurality of ranking levels pre-defined by a plurality of standard values of the abdominal visceral fat cross sectional area VA. In this configuration, a quantitative value of an abdominal visceral fat cross sectional area VA of a subject can be visually seen and easily interpreted through the ranking level shown on the display.

Furthermore, according to the visceral fat determining device of the present invention, the abdominal girth $W_L$ is a circumferential length of an abdomen at $4^{th}$ lumbar vertebrae of the subject. The abdominal girth $W_L$ at $4^{th}$ lumbar vertebrae of the subject is most strongly correlated with the state of the visceral fat of the subject.

Furthermore, the visceral fat determining device of the present invention can be provided with means for measuring the abdominal girth $W_L$ of a subject. In this constitution, the abdominal girth of the subject can be conveniently measured timely and on-demand. Therefore, use of the means above mentioned can eliminate the need for inputting the abdominal girth $W_L$ of a subject measured elsewhere.

Furthermore, according to the present invention, the visceral fat determining device can be configured in such a way that the abdominal girth $W_L$ measured by the size measuring means is directly inputted into the data processing unit. In this configuration, a subject does not need to input the required abdominal girth $W_L$ through the input means.

BEST MODE FOR CARRYING OUT THE INVENTION

Figure 1A:
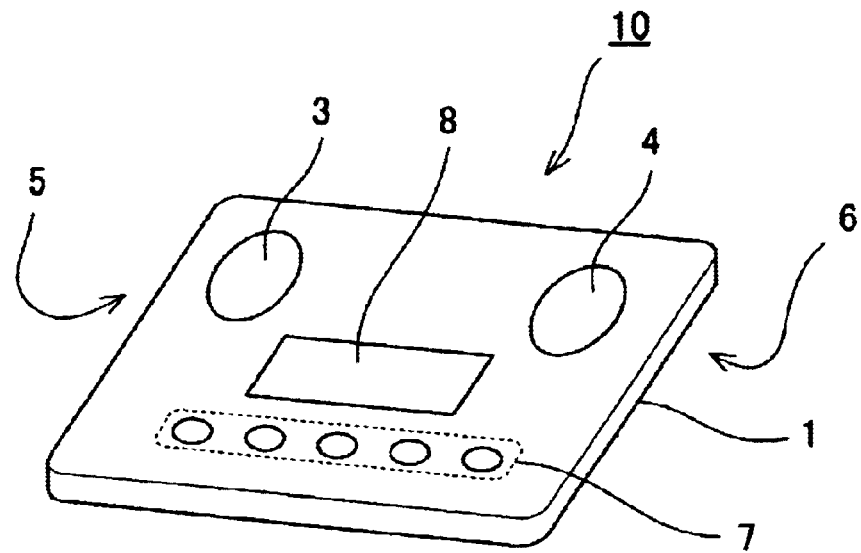
FIG. 1A is a perspective view of an example of a visceral fat determining device.
Figure 1B:
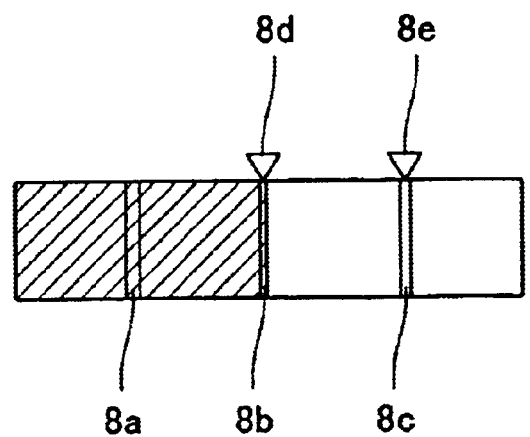
FIG. 1B is a view representing an example of a display of the visceral fat determining device.

A preferred embodiment of the present invention will be described referring to FIGS. 1A–6. FIGS. 1A, 1B show a visceral fat determining device 10 as an example of a preferred embodiment of the present invention. FIG. 1A is a perspective view of the visceral fat determining device 10. The visceral fat determining device 10 is capable of obtaining visceral fat information of a subject such as an estimated value of an abdominal visceral fat cross sectional area VA which is a cross sectional area of the visceral fat at the abdomen and a total abdominal fat cross sectional area WA including abdominal subcutaneous fat. The device is provided with a built-in body fat determining device so that the body fat ratio FAT can also be measured.

Furthermore, with the visceral fat determining device 10, BMI can be also obtained, which has been conventionally used as an index of obesity. The BMI can be obtained through a well-known formula based on the subject's height and weight as part of personal data to be described later.

The visceral fat determining device 10 is provided with an operation portion 7 including a plurality of keys to be used for inputting numerical values, letters, and etc. With these keys, the personal data representing physical characteristics of the subject can be inputted. Therefore, a plurality of keys necessary for inputting the personal data are provided. That is, the operation portion 7 corresponds to serve as means for inputting the personal data.

The personal data to be inputted into the visceral fat determining device 10 include height, weight, sex, age, and waist size (hereinafter, referred to as abdominal girth) of the subject. As the abdominal girth $W_L$, a circumferential length of an abdomen at $4^{th}$ lumbar vertebrae of the subject is preferred because it is strongly correlated with the state of the visceral fat of the subject.

Furthermore, the personal data to be inputted may include a thickness of abdominal subcutaneous fat s of the subject, which can be measured using a number of well known subcutaneous fat thickness measuring means such as a caliper, an ultrasonic probe, and so on.

Moreover, the thickness of abdominal subcutaneous fat s of the subject to be inputted into the visceral fat determining device may be the value at the side umbilical region, the value at the ilium upper part, the sum, or an average of the sum.

The operation portion 7 is provided with a number of keys such as a selection key for selecting items of the personal data and numeric keys for inputting values. Furthermore, the operation portion 7 is also provided with an ON/OFF power switch for turning on and off the visceral fat determining device 10 and an impedance measurement starting switch for starting a measurement of a bioelectrical impedance Z to be explained later.

Furthermore, with the operation portion 7, a plurality of measurement modes can be selected for the abdominal visceral fat cross sectional area VA. In accordance with the selected mode, a corresponding measurement routine such as a first measurement routine and a second measurement routine that will be described later is executed.

A display portion 8 displays the personal data inputted through the operation portion 7 and BMI derived from the inputted personal data, as well as measurement results such as body fat ratio FAT and values of the abdominal visceral fat cross sectional area VA. FIG. 1B is a view of an example of the display on the display portion 8.

In FIG. 1B, the measurement result of the abdominal visceral fat cross sectional area VA is shown as rated into a plurality of ranking levels. Those indicated by 8a, 8b, and 8c in FIG. 1B are the ranking bars. A plurality of standard values of the abdominal visceral fat cross sectional area VA are set forth in advance and then compared with the measured value of the abdominal visceral fat cross sectional area VA of a subject to determine the rank to which the measured value of the subject is rated. According to the example given in FIG. 1B, the display shows that the abdominal visceral fat cross sectional area VA of the subject corresponds to the ranking bar 8b.

Furthermore, as shown in FIG. 1B, level indicators 8d and 8e can also be displayed. The level indicators 8d and 8e may be correlated with specific symptoms related to the visceral fat. For example, if the abdominal visceral fat cross sectional area VA of a person is larger than 100 $cm^2$, the person may be clinically diagnosed to be obese. Therefore, the level indicator 8e, may be set to correspond to 100 $cm^2$ of the abdominal visceral fat cross sectional area VA.

As shown in FIG. 1B, displaying the measured results obtained as a quantitative value in accordance with the ranking level or displaying the relevant information about a symptom from which the person might be suffering in accordance with the measured result allow visual, stepwise, and lucid interpretation of the results.

Furthermore, the visceral fat determining device 10 is provided with body fat ratio measuring means for measuring a body fat ratio FAT of the subject as described later. That is, an electrode 3 is provided on the left side of a front portion of the top surface of the visceral fat determining device 10. An electrode 4 is disposed on the right side of the front portion.

And, an electrode 5 is provided on a portion of a reverse surface of a main body 1 which substantially corresponds to the portion where the electrode 3 is provided. An electrode 6 is provided on a portion of the reverse surface that substantially corresponds to the portion where the electrode 4 is provided.

A group of electrodes comprising the electrodes 3, 4, 5, and 6 serve as means for measuring the bioelectrical impedance Z of a human body. And, the electrodes 5 and 6 serve as a pair of current path forming electrodes which form an electric current path within the body of the subject, and the electrodes 3 and 4 serve as a pair of voltage measurement electrodes which measure electric potential difference across two points in the path.

And, these groups of electrodes are connected to impedance measuring means (not shown) that is well known in the art of body fat determining device and incorporated in to the main body 1. Specifically, the electrodes 5 and 6 are connected to the portion of an electric circuit serving as a constant current source that outputs a constant current, whereas the electrodes 3 and 4 are connected to the portion of another electric circuit serving as a voltmeter.

When measuring the bioelectrical impedance Z of the subject, the thumb and the index finger of the left hand of the subject are respectively attached to the electrodes 3 and 5. In a similar way, the thumb and the index finger of the right hand of the subject are respectively attached to the electrodes 4 and 6. In this way, the bioelectrical impedance Z of the subject through the hands serving as the extremities of the body can be measured.

As embodied in the visceral fat determining device 10, advantageously, the configuration of the electrode 5 on the portion of the reverse surface which substantially corresponds to the portion where the electrode 3 is provided and the electrode 6 on a portion of the reverse surface which substantially corresponds to the portion where the electrode 4 is provided allows the subject to stably hold the visceral fat determining device 10 with the two fingers of each hand in contact with the respective electrodes without any difficulty.

That is, while the visceral fat determining device 10 is stably held with the hands, the bioelectrical impedance Z can be steadily measured. Furthermore, the electrodes 3 and 5 can be pressed with the two fingers from one hand, and the electrodes 4 and 6 can be pressed with the two fingers from the other hand of the subject with substantially even forces. In this way, the bioelectrical impedance can be more stably measured.

Figure 2:
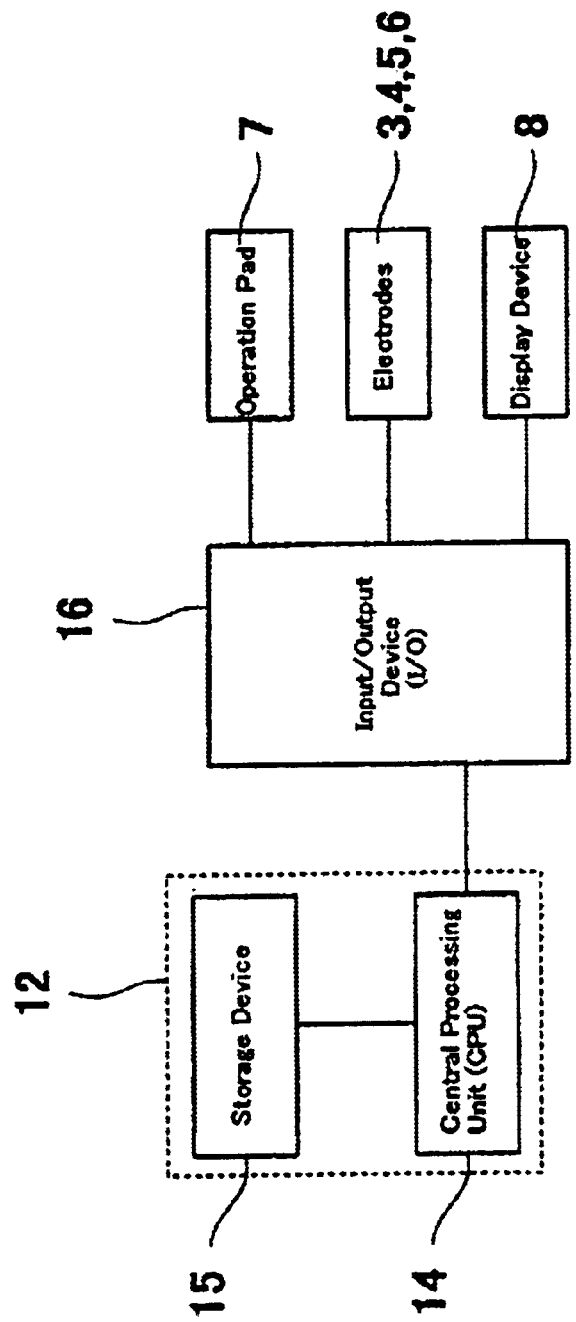
FIG. 2 is a schematic block diagram representing a signal processing in the visceral fat determining device.

Referring to FIG. 2, a block diagram representing signal processing in the visceral fat determining device 10 is described. Various types of calculations can be performed by a data processing unit 12 including a central processing unit (CPU) 14 and a storage device 15.

The personal data inputted through the function keys provided in the operation portion 7 and measured values of the bioelectrical impedance Z obtained with the electrodes 3, 4, 5, and 6 are all stored in the storage device 15. Furthermore, the storage device 15 stores various kinds of formulae, coefficients, and etc. necessary for obtaining the body fat ratio FAT based on the bioelectrical impedance Z and the personal data. Even furthermore, the body fat ratio FAT is thus calculated, the result is stored in the storage device 15. Still furthermore, when a value of the BMI and an estimated value of the abdominal visceral fat cross sectional area VA are obtained, they are stored in the storage device 15.

Furthermore, the storage device 15 stores an operation instruction routine including procedures necessary for giving the subject required guidance and instructions on how to operate the visceral fat determining device 10 and an measurement routine including procedures for calculating BMI, the body fat ratio FAT, and the estimated values of the abdominal visceral fat cross sectional area VA. This measurement routine includes a first measurement routine and a second measurement routine as described later in an execution example of the measurement routine.

Furthermore, the storage device 15 stores a first regression coefficient $a_1$, of the abdominal girth $W_L$, a second regression coefficient $a_2$ of the abdominal girth $W_L$, a third regression coefficient $a_3$ of the abdominal girth $W_L$, a fourth regression coefficient $a_4$ of the abdominal girth $W_L$, a fifth regression coefficient $a_5$ of the abdominal girth $W_L$, an eighth regression coefficient $a_8$ of the abdominal girth $W_L$, a ninth regression coefficient $a_9$ of the abdominal girth $W_L$, a first regression coefficient $f_1$, of the abdominal girth index, a first regression coefficient $b_1$, of BMI, a second regression coefficient $d_2$ of BMI, a first regression coefficient $b_1$ of the body fat ratio FAT, a second regression coefficient $d_2$ of the body fat ratio FAT, a third regression coefficient $d_3$ of the body fat ratio FAT, a fourth regression coefficient $d_4$ of the body fat ratio FAT, a fifth regression coefficient $d_5$ of the body fat ratio FAT, a first regression coefficient $e_1$ of the thickness of abdominal subcutaneous fat s, a second regression coefficient $e_2$ of the thickness of abdominal subcutaneous fat s, a first regression constant $c_1$, a second regression constant $c_2$, a third regression constant $c_3$, a fourth regression constant $c_4$, a fifth regression constant $c_5$, a sixth regression constant $c_6$, an eleventh regression constant $c_{11}$, a twelfth regression constant $c_{12}$, a thirteenth regression constant $c_{13}$, and a fourteenth regression constant $c_{14}$.

Furthermore, the storage device 15 stores a first regression coefficient $g_1$ for the bioelectrical impedance Z, and the first regression coefficient $j_1$ for the term $(T_L^2/Z)$, obtained by dividing a square of a height $T_L^2$ by the bioelectrical impedance Z.

Furthermore, the storage device 15 stores a first regression coefficient $h_1$ for the term $(W_L^2 \cdot T_L \cdot FAT)$, obtained by multiplying a square of the abdominal girth $W_L^2$, the height $T_L$, and the body fat ratio FAT, and the first regression coefficient $i_1$ for the term $(W_L^2 \cdot T_L \cdot age)$, obtained by multiplying a square of the abdominal girth $W_L^2$, height $T_L$, and age.

Furthermore, the storage device 15 stores a second regression coefficient $i_2$ for the term $(W_L^2 \cdot T_L \cdot age)$, obtained by multiplying a square of an abdominal girth $W_L^2$, height $T_L$, and age.

These regression coefficients and constants $a_1$, $a_2$, $a_3$, $a_4$, $a_5$, $a_8$, $a_9, b_1$, $b_2 c_1, c_2$, $c_3$, $c_4$, $c_5$, $c_6$, $c_{11}$, $c_{12}$, $c_{13}$, $c_{14}$, $d_1$, $d_2$, $d_5$, $e_1$, $e_2$, $f_1$, $g_1$, $h_1$, $i_1$, $i_2$, and $j_1$ are obtained elsewhere and then inputted to the visceral fat determining device 10 for storage.

These regression coefficients and constants are obtained in the following procedure. Specifically, the actual abdominal visceral fat cross sectional area VA of each of a number of individuals who are randomly selected is measured. In addition, the abdominal girth $W_L$, the BMI, the bioelectrical impedance Z, the body fat ratio FAT, the thickness of abdominal subcutaneous fat s, and the height $T_L$ of each of the individuals are also measured.

The first regression coefficient $a_1$ of the abdominal girth $W_L$ and the first regression constant $c_1$ can be obtained by statistically correlating the abdominal girth $W_L$ with the actually measured abdominal visceral fat cross sectional area VA. Also, the second regression coefficient $a_2$ of the abdominal girth $W_L$, the first regression coefficient $b_1$ of the BMI, and the second regression constant $c_2$ can be obtained by statistically analyzing correlation between the abdominal girth $W_L$, the BMI, and the actually measured abdominal visceral fat cross sectional area VA. Moreover, the third regression coefficient $a_3$ of the abdominal girth $W_L$, the first regression coefficient $d_1$ of the body fat ratio FAT, and the third regression constant $c_3$ can be obtained by statistically analyzing correlation between the abdominal girth $W_L$, the body fat ratio FAT, and the actually measured abdominal visceral fat cross sectional area VA.

Also, the fourth regression coefficient $a_4$ of the abdominal girth $W_L$, the second regression coefficient $b_2$ of the BMI, the first regression coefficient $e_1$ of the thickness of abdominal subcutaneous fat s, and the fourth regression constant $c_4$ can be obtained by statistically analyzing correlation between the abdominal girth $W_L$, the BMI, the thickness of abdominal subcutaneous fat s and the actually measured abdominal visceral fat cross sectional area VA. What is more, the fifth regression coefficient $a_5$ of the abdominal girth $W_L$, the second regression coefficient $d_2$ of the body fat ratio FAT, the second regression coefficient $e_2$ of the thickness of abdominal subcutaneous fat s, and the fifth regression constant $c_5$ can be obtained by statistically analyzing correlation between the abdominal girth $W_L$, the body fat ratio FAT, the thickness of abdominal subcutaneous fat s, and the actually measured abdominal visceral fat cross sectional area VA.

Even furthermore, the first regression coefficient $f_1$ of the abdominal girth index, and the sixth regression constant $c_6$ can be obtained by statistically correlating the abdominal girth index obtained by dividing the square of the abdominal girth $W_L$ by the height with the actually measured abdominal visceral fat cross sectional area VA.

Also, the eighth regression coefficient $a_8$ of the abdominal girth $W_L$, the first regression coefficient $j_1$ for the term $(T_L^2/Z)$, and the eleventh regression constant $c_{11}$ can be obtained by statistically analyzing correlation between the abdominal girth $W_L$, the term $(T_L^2/Z)$, and the actually measured abdominal visceral fat cross sectional area VA.

Also, the ninth regression coefficient $a_9$ of the abdominal girth $W_L$, the first regression coefficient $g_1$ for the impedance Z, and the twelfth regression constant $c_{12}$ can be obtained by statistically analyzing correlation between the abdominal girth $W_L$, the impedance Z, and the actually measured abdominal visceral fat cross sectional area VA.

Also, the first regression coefficient $i_1$ for the term $(W_L^2 \cdot T_L \cdot \text{age})$, the first regression coefficient $h_1$ for the term $(W_L^2 \cdot T_L \cdot \text{FAT})$, and the thirteenth regression constant $c_{13}$ can be obtained by statistically analyzing the term $(W_L^2 \cdot T_L \cdot \text{age})$, the term $(W_L^2 \cdot T_L \cdot \text{FAT})$, and the actually measured abdominal visceral fat cross sectional area VA.

More specifically, the first regression coefficient $i_1$ for the term $(W_L^2 \cdot T_L \cdot \text{age})$, the first regression coefficient $h_1$ for the term $(W_L^2 \cdot T_L \cdot \text{FAT})$, and the thirteenth regression constant $c_{13}$ are statistically determined based on human bodies of a number of male subjects who are randomly selected. That is, these coefficients $i_1$, $h_1$, and $c_{13}$ are, as described later, used in a formula to calculate the estimated value of the abdominal visceral fat cross sectional area VA of the male subject.

The second regression coefficient $i_2$ for the term $(W_L^2 \cdot T_L \cdot \text{age})$, the fifth regression coefficient $d_5$ of the body fat ratio FAT, and the fourteenth regression constant $c_{14}$ can be obtained by statistically analyzing correlation between the term $(W_L^2 \cdot T_L \cdot \text{age})$, the body fat ratio FAT, and the abdominal visceral fat cross sectional area VA.

More specifically, the second regression coefficient $i_2$ for the term $(W_L^2 \cdot T_L \cdot \text{age})$, the fifth regression coefficient $d_5$ of the body fat ratio FAT, and the fourteenth regression constant $c_{14}$ are statistically determined based on human bodies of a number of female subjects who are randomly selected. That is, these coefficient $i_2$, $d_5$, and $c_{14}$ are, as described later, used in a formula to calculate the estimated value of the abdominal visceral fat cross sectional area VA of the female subjects. In order to determine these coefficients from $a_1$ to $j_1$, the actually measured abdominal visceral fat cross sectional area VA can be statistically correlated with personal data of each individual subject by means of a regression analysis. For example, the first regression coefficient $a_1$ of the abdominal girth $W_L$ and the first regression constant $c_1$ can be obtained by single regression analysis based on an assumption that the actually measured abdominal visceral fat cross sectional area VA is exclusively correlated with the abdominal girth $W_L$. Furthermore, when there is a correlation between the abdominal girth $W_L$, other personal data, and actually measured abdominal visceral fat cross sectional area VA, then the coefficients can be obtained by multiple regression analysis.

The abdominal visceral fat cross sectional area VA of human bodies of random samples is actually obtained through tomography. This tomography can be provided with a plurality of different means such as CT scanning, MRI, ultrasonic diagnosis, and any other methods capable of performing accurate measurements of human abdominal cross sections. Furthermore, in determining the coefficients from $a_1$ to $j_1$, the number of subjects required for statistically analyzing the abdominal visceral fat cross sectional area VA should preferably be more than 100, more preferably more than 500.

Referring to a block diagram representing the signal processing in the visceral fat determining device 10 in FIG. 2, the data and measured values stored in the storage device 15 can be displayed on the display portion 8. Furthermore, the data and measured values are inputted/outputted to/from the central processing unit 14 and the storage device 15 through an input/output device 16 for further processing.

Figure 3:
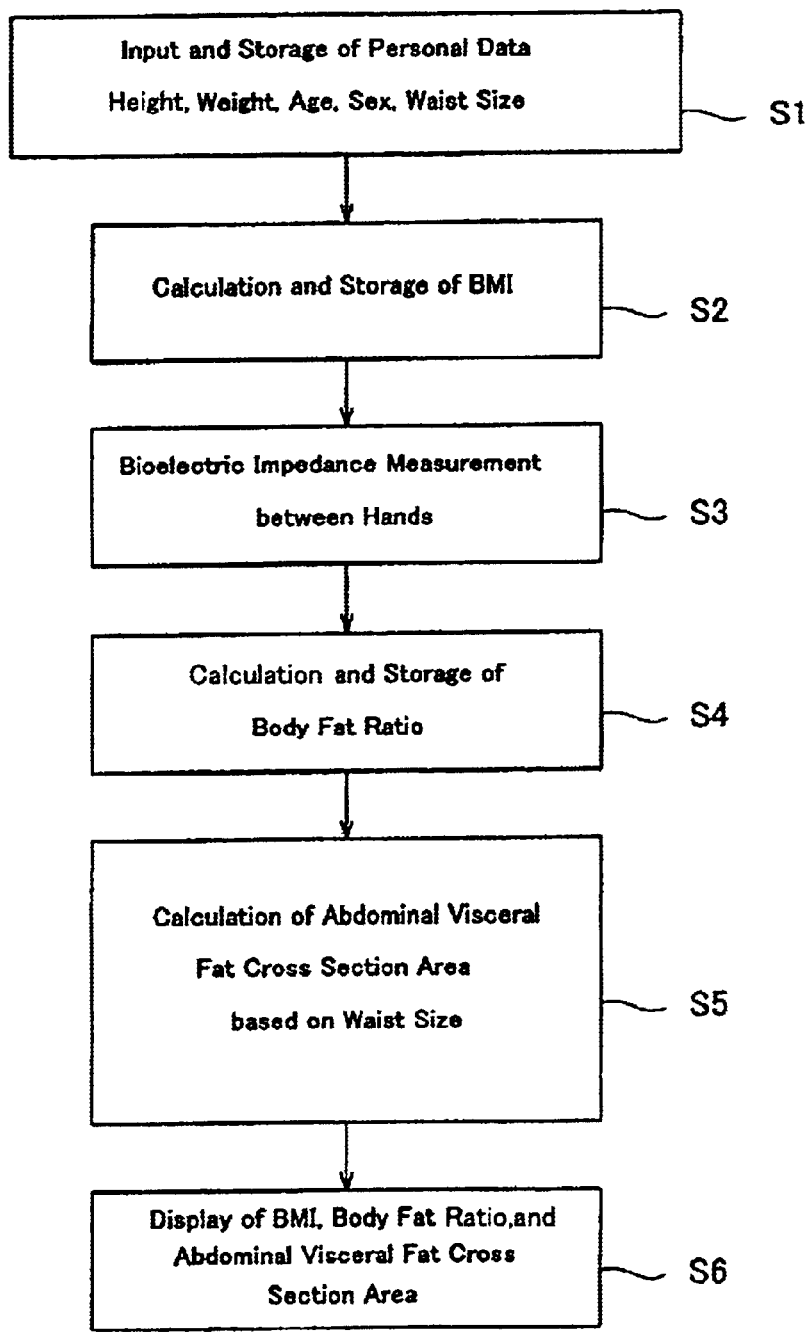
FIG. 3 is a flow chart representing an example of procedures required to measure an abdominal visceral fat cross sectional area.

Referring to FIG. 3, an example of the operation of the visceral fat determining device 10 will be described. The visceral fat determining device 10 is turned on, and when selection of the first measurement mode is made through the operation portion 7, the first measurement routine is started.

First, the personal data which is body specific information including the height, weight, age, sex, and abdominal girth $W_L$ of a subject are inputted by the subject and stored (S1).

BMI is then calculated based on the height and weight inputted in (S1) and stored (S2). A bioelectrical impedance Z between the hands of the subject is measured (S3), and the resulting bioelectrical impedance Z is stored. Then, a body fat ratio FAT is calculated using required data from the inputted personal data and the bioelectrical impedance Z and stored (S4). Abdominal visceral fat cross sectional area VA is estimated by calculation using the abdominal girth $W_L$ (S5), and the obtained BMI, the body fat ratio FAT, and the abdominal visceral fat cross sectional area VA are displayed on the display portion 8 (S6).

The estimated value of the abdominal visceral fat cross sectional area VA in (S5) is calculated with formula (1).

$$VA = a_1 \cdot W_L + c_1 \tag{1}$$

In procedure S5 shown in FIG. 3, abdominal visceral fat cross sectional area VA is assumed to exclusively correlate with the abdominal girth $W_L$ of the subject, and the estimated value of VA is calculated using the coefficients of a1 and c1 and the abdominal girth $W_L$.

The formula (1) may be replaced by the following formulae from (2) to (5) to calculate.

$$VA = a_2 \cdot W_L + b_1 \cdot BMI + c_2 \tag{2}$$

$$VA = a_3 \cdot W_L + d_1 \cdot FAT + c_3 \tag{3}$$

$$VA = a_4 \cdot W_L + b_2 \cdot BMI + e_1 \cdot s + c_4 \tag{4}$$

$$VA = a_5 \cdot W_L + d_2 \cdot FAT + e_2 \cdot s + c_5 \tag{5}$$

$$VA = a_8 \cdot W_L + j_1 \cdot (T_L^2 / Z) + c_{11} \tag{6}$$

$$VA = a_9 \cdot W_L + g_1 Z + c_{12} \tag{7}$$

In formula (2), the estimated value of VA is calculated based on the assumption that the VA is exclusively correlated with the abdominal girth $W_L$ and BMI of the subject. In formula (3), the VA is calculated based on the assumption that the VA is exclusively correlated with the abdominal girth $W_L$ and the body fat ratio FAT of the subject.

In formula (4), the estimated value of VA is calculated based on the assumption that the VA is exclusively correlated with the abdominal girth $W_L$, BMI, and thickness of abdominal subcutaneous fat s of the subject. In formula (5), the estimated value of VA is calculated based on the assumption that the VA is exclusively correlated with the abdominal girth $W_L$, the body fat ratio FAT, and the thickness of abdominal subcutaneous fat s of the subject.

In formula (6), the estimated value of VA is calculated based on the assumption that the VA is exclusively correlated with the abdominal girth $W_L$ and the term $(T_L^2/Z)$ obtained by dividing the square of the height $T_L^2$ by the impedance Z of the subject. In formula (7), the estimated value of VA is calculated based on the assumption that the VA is exclusively correlated with the abdominal girth $W_L$ and the impedance Z of the subject.

As should be understood from the above, while, in the formula (1), the estimated value of VA is calculated based on the correlation with the abdominal girth $W_L$, in the formulae from (2) to (7), the estimated value of VA is calculated based on the correlation with a plurality of terms of the personal data. Therefore, the formulae from (2) to (7), with the correlation of a plurality of values of the personal data, can provide the estimated value of VA with more precise reflection of the physical characteristics of the individual subject.

In the formula (4) or (5) including the thickness of abdominal subcutaneous fat s, the estimated value of VA can reflect the thickness of abdominal subcutaneous fat of the subject.

On the other hand, the calculation of an estimated value of VA using the formulae (1)–(3), (6) and (7) has the following advantage. Since the formulae do not include inputting the thickness of the abdominal subcutaneous fat s, the burdensome procedure of measuring the thickness of the abdominal subcutaneous fat with means such as a caliper or the like may be avoided.

The estimated value of VA can be calculated based on the assumption that the VA is exclusively correlated with the abdominal girth index. In formula (8), the estimated value of VA can be calculated based on the correlation with an abdominal girth index.

$$VA = f_1 \cdot (W_L^2/T_L) + c_6 \tag{8}$$

In the formula (8), $T_L$ is height of the subject. The abdominal girth index can be obtained by the term $(W_L^2/T_L)$. According to the formula (8), the estimated value of VA can be calculated based on the correlation with the abdominal girth index known to highly correlate with the obesity.

Also, the estimated value of VA can be calculated based on the correlation with the terms $(W_L^2 \cdot T_L \cdot age)$ and $(W_L^2 \cdot T_L \cdot FAT)$. In formula (9), the estimated value of VA can be calculated based on the correlation with the terms $(W_L^2 \cdot T_L \cdot age)$ and $(W_L^2 \cdot T_L \cdot FAT)$.

$$VA = i_1 \cdot W_L^2 \cdot T_L \cdot age + h_1 \cdot W_L^2 \cdot T_L \cdot FAT - c_{13}$$

With the formula (9), the estimated value of VA can be more accurately calculated when the subject is male. Therefore, in the case where "male" is entered as the sex of the subject through the operation portion 7, the formula (9) should be chosen to accurately calculate the estimated value of VA for the male subject.

Also, the estimated value of VA can be calculated based on the correlation with the term $(W_L^2 \cdot T_L \cdot age)$ and the body fat ratio FAT. In formula (10), the estimated value of VA can be calculated based on the correlation with the term $(W_L^2 \cdot T_L \cdot age)$ and body fat ratio FAT.

$$VA = i_2 \cdot W_L^2 \cdot T_L \cdot age + d_5 \cdot FAT - c_{14} \tag{10}$$

With the formula (10), the estimated value of VA can be more accurately calculated when a subject is a female. Therefore, in the case where "female" is entered as the sex of the subject through the operation portion 7, the formula (10) should be chosen to accurately calculate the estimated value of VA for the female subject.

Also, each of the formulae from (1) to (10) may include correction terms on the basis of age and sex. The age correction term Yc is given by formula (11), and the sex correction term Xc is given by formula (12).

$$Yc = -\delta \cdot age \tag{11}$$

$$Xc = \eta \cdot sex \tag{12}$$

In the formula (11), "age" is the age of the subject, and $\delta$ is an age correction coefficient. Also, in the formula (12), "sex" is a variable depending on the sex of the subject, and $\eta$ is a sex correction coefficient. In the case that these correction terms are included in the formulae from (1) to (10), they are defined and treated as variable terms of the multiple regression equation. Therefore, $\delta$ and age are defined as a regression coefficient and a variable respectively in the formula (11). Also, $\eta$ and sex are defined as a regression coefficient and a variable respectively in the formula (12). These are obtained based on correlation with the estimation formulae for VA.

Addition of the correction terms Xc given by the formula (11) and Yc given by the formula (12) to the formulae from (1) to (10) in the calculation of VA makes it possible to more precisely reflect the personal physical characteristics of the subject in terms of the age and sex. Either one or both of the correction terms Xc and Yc may be added to the formulae from (1) to (10). If both of the terms Xc and Yc are added in the calculation of VA using any one of the formulae from (1) to (10), it becomes possible to obtain the VA with more precise reflection of the personal physical characteristics of the subject.

Further, the amount of the abdominal visceral fat can be calculated based on the abdominal visceral fat cross sectional area VA thus obtained.

Figure 4:
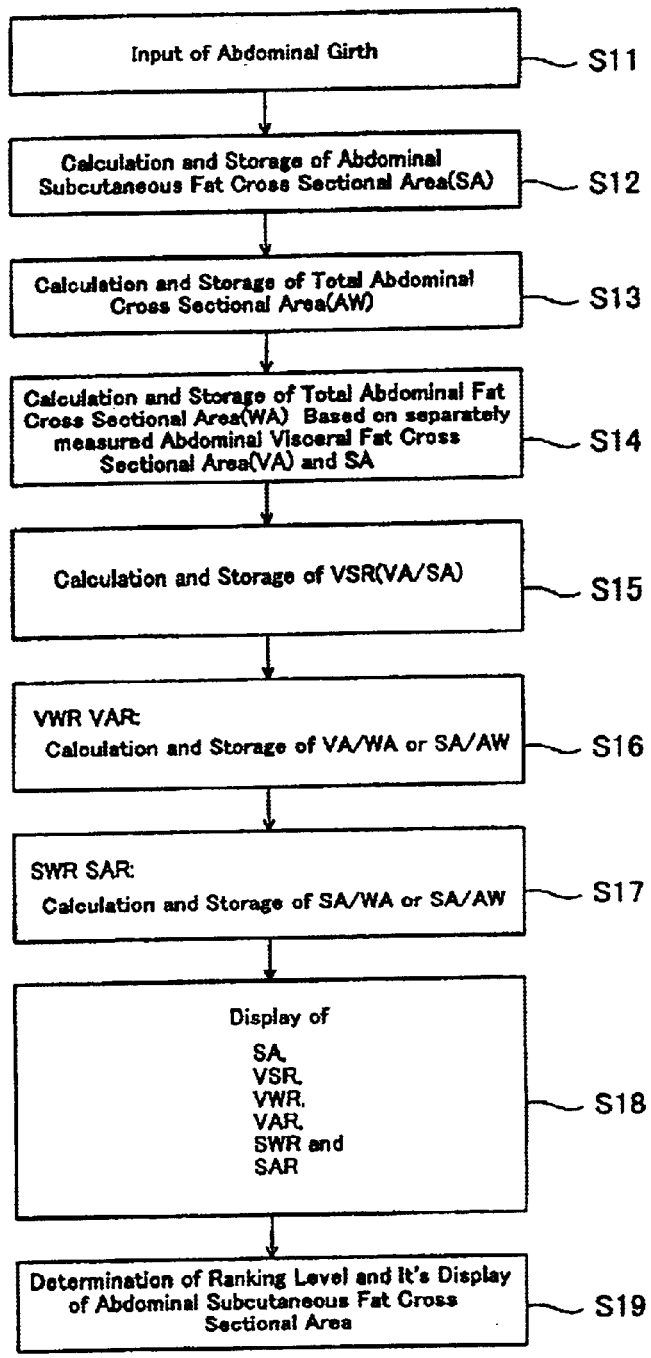
FIG. 4 is a flow chart representing an example of procedures required to measure an abdominal visceral fat cross sectional area.

Next, referring to FIG. 4, another operation example of the visceral fat determining device 10 will be described. When the second measurement mode is selected through the operation portion 7, then the second measurement routine is started. First, a circumferential length of a torso of a subject as the abdominal girth $W_L$ is inputted by the subject (S11). Then, the subcutaneous fat cross sectional area (SA) is calculated and stored (S12). In step (S12), the calculation of the SA is performed by using the following formula (15).

$$SA = W_L \cdot s - \pi \cdot s^2 \tag{15}$$

In the formula (15), $W_L$ is the circumferential length of the abdomen and s is the thickness of the abdominal subcutaneous fat of the subject.

Then, a total abdominal cross sectional area AW is calculated and stored (S13).

In step (S13), AW is calculated by using the following formula (16).

$$AW = \zeta \cdot (W_L^2/4\pi) \tag{16}$$

In formula (16), $\pi$ is the circular constant pi. $\zeta$ is a conversion coefficient for a conversion between circular and oval circumferences.

Then, based on the abdominal visceral fat cross sectional area VA and SA, the total abdominal fat cross sectional area WA is calculated and stored (S14). In step (S14), the WA is calculated by using the following formula (17).

$$WA = VA + SA \tag{17}$$

Then, VSR, a ratio of the abdominal visceral fat cross sectional area VA to the abdominal subcutaneous fat cross sectional area SA, is calculated and stored (S15). In step (S15), VSR is calculated by using the following formula (18).

$$VSR = VA/SA \tag{18}$$

Then, a VWR which is a ratio of the abdominal visceral fat cross sectional area VA to the total abdominal fat cross sectional area WA and a VAR which is a ratio of the abdominal visceral fat cross sectional area VA to the total abdominal fat cross sectional area AW are calculated and stored (S16). In step (S16), VWR and VAR are calculated by using the following formulae (19) and (20) respectively.

$$VWR = VA/WA \quad (19)$$

$$VAR = VA/AW \quad (20)$$

Then, a SWR, a ratio of the abdominal subcutaneous fat cross sectional area SA to the abdominal total fat cross sectional area of WA, and a SAR, a ratio of the abdominal subcutaneous fat cross sectional area SA to the total abdominal cross sectional area AW, are calculated and stored (S17). In step (S17), SWR and SAR are calculated by using the following formulae (21) and (22) respectively.

$$SWR = SA/WA \quad (21)$$

$$SAR = SA/AW \quad (22)$$

Then, calculated values of SA, VSR, VWR, VAR, SWR, and SAR are displayed on the display portion 8 (S18). Furthermore, the abdominal subcutaneous fat cross sectional area SA is rated in a plurality of ranking levels and displayed on the display portion 8 in accordance with the ranking (S19).

Figure 5A:
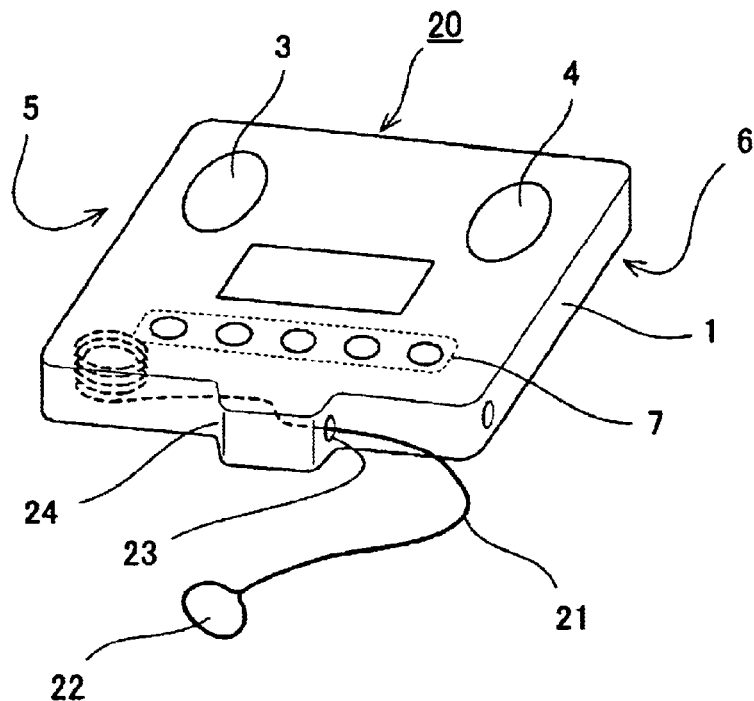
FIG. 5A is a view representing a visceral fat determining device provided with a size measuring means, shown in a partially extended configuration.

In the above description referring to FIGS. from 1A to 4, the abdominal girth $W_L$ of the personal data of the subject was measured elsewhere and then inputted in through the operation portion 7. Alternatively, the visceral fat determining device may be provided with size measuring means capable of measuring the abdominal girth of the subject. FIG. 5A is a perspective view including a partial see-through portion of a visceral fat determining device 20 as an example of such a visceral fat determining device with the size measuring means.

This visceral fat determining device 20 is provided with a measuring tape 21 serving as the size measuring means, which can be drawn in and pulled out of the main body. This measuring tape 21 can be grabbed with a pull tip 22 at its end and then pulled to draw it out of a pull portion 23. Furthermore, this measuring tape 21 can be stored in the main body by using a storage button (not shown) provided with the visceral fat determining device 20.

Figure 5B:
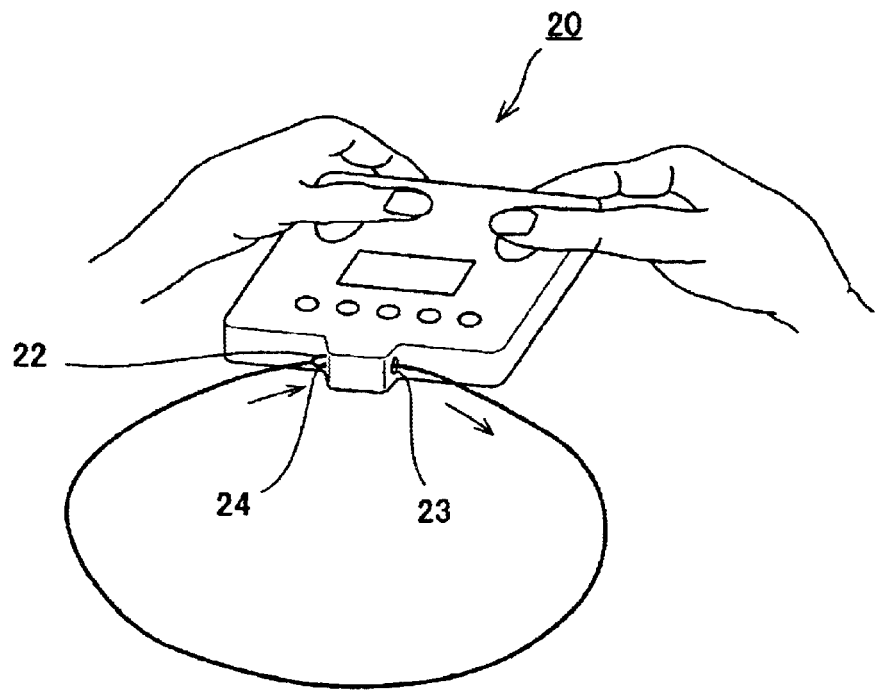
FIG. 5B is a view representing a visceral fat determining device provided with a size measuring means, shown in a loop configuration.

Furthermore, an engaging portion 24 is provided on the opposite side of the pull portion 23 that is formed on the tip portion of the visceral fat determining device 20. As shown in FIG. 5B, by hooking the pull tip 22 on the engaging portion 24, the measuring tape 21 can accurately measure body sizes of a subject without sagging.

Even furthermore, as FIG. 5B illustrates, the size of a required portion of the subject's body can be measured by pulling out the measuring tape 21, winding it around the body (e.g., the abdomen and the buttock), and hooking the pull tip 22 on the engaging portion 24.

While the abdominal girth $W_L$ of the subject measured with the measuring tape 21 can be inputted in through the operation portion 7, it may also be directly inputted into the data processing unit 12 without going through the operation portion 7. In this case, size data obtained by the measuring tape 21 should be processed as a digital signal and inputted into the data processing unit 12 through the input/output (I/O) device 16 in the signal processing block as shown in FIG. 2.

As exemplified by the visceral fat determining device 20, if provided with the size measuring means is provided so that the abdominal girth $W_L$ of the subject can be measured on demand, can more accurately provide the estimated value of the abdominal visceral fat cross sectional area VA based on the latest abdominal girth $W_L$ since the measurement can be performed right at the time when the abdominal visceral fat cross sectional area is to be measured.

While the visceral fat determining device 20 is provided with the measuring tape 21 as the means for measuring the abdominal girth $W_L$ of the subject, it may also be provided with a roller (not shown here) that serves as a rolling distance determining device. Specifically, the size measuring means can be provided by a roller which is rolled on and along a portion of the subject's body to be measured, and the size is obtained from the travel distance of the roller obtained from the number of roller rotations. Use of such a rolling type odometer as the size measuring means makes the measure of the abdominal girth $W_L$ of the subject easy since rolling the roller on and along the waist of the subject is all it requires.

In the preceding examples of the visceral fat determining device 10 and the visceral fat determining device 20, the measurement of the bioelectrical impedance Z related to the body fat ratio FAT of the subject is performed through the hands.

Figure 6:
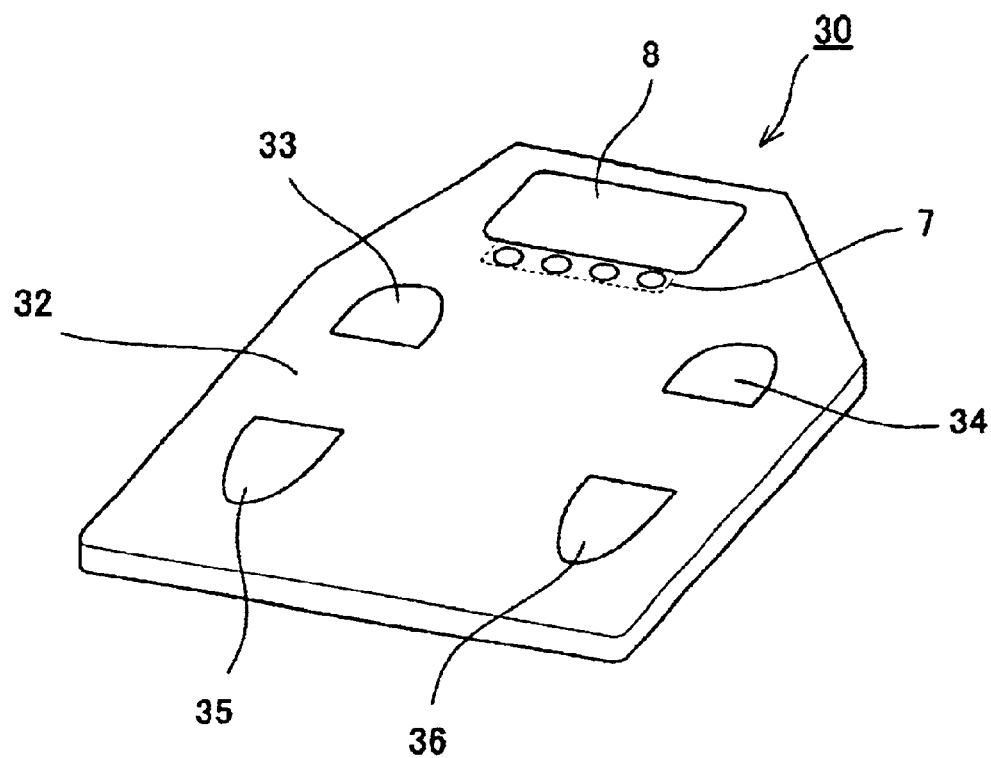
FIG. 6 is a perspective view of an example of a visceral fat determining device.

The visceral fat determining device according to the present invention may be integrated with a weight scale and a body fat determining device. Specifically, a visceral fat determining device 30 shown in FIG. 6 is provided with a weight scale and a body fat determining device.

A main body of the visceral fat determining device 30 has a top surface formed with a weight measuring surface 32, and a load cell is provided inside the visceral fat determining device to measure the weight of the subject on the surface (not shown here). Therefore, the weight of the subject can be measured when the subject stands on the weight measuring surface 32.

Furthermore, electrodes 33, 34, 35, and 36 are provided on the weight measuring surface 32 for measuring the bioelectrical impedance Z of the subject. The electrodes 33 and 34 serve as a pair of current path forming electrodes for developing an electric current path in the body of the subject through which electric current is flown. Electrodes 35 and 36 serve as a pair of voltage measurement electrodes for measuring the electric potential difference between two points across the path.

As in the visceral fat determining devices 10 and 20, the electrodes 33, 34, 35, and 36 are connected to impedance measuring means in the main body that is well known in the art of body fat determining device. Therefore, the body's impedance can be measured through the electrodes 33, 34, 35, and 36.

When the subject stands on the weight measuring surface 32 of the visceral fat determining device 30 with the sole of the left foot being in contact with the electrodes 33 and 35 and the sole of the right foot being in contact with the electrodes 34 and 36, the weight and the bioelectrical impedance Z of the subject with the feet representing the ends of the body are simultaneously measured.

The visceral fat determining device 30 is provided with the operation portion 7 and the display portion 8 which are constituted similarly to those of the visceral fat determining device 10 described above and with the data processing unit 12 which includes the central processing unit 14 and the storage device 15.

Furthermore, the storage device 15 is designed in the same way as the device in visceral fat determining device 10 and stores the routines, the coefficients, and data, and inputted data and measurement results. Moreover, signals are processed in the same way as described referring to FIG. 2.

In the visceral fat determining device 30, the weight of the subject measured with the load cell provided inside the main body is automatically processed as weight data by the data processing unit 12. Therefore, instead of inputting the weight data as one of the personal data through the operation portion 7, the weight data measured with the visceral fat determining device 30 can be used.

Furthermore, the size measuring means as described for the visceral fat determining device 20 can be installed in the visceral fat determining device 30, thereby making it possible to measure the waist size of the subject at the same time as the weight measurement.

While the visceral fat determining device 30 described above is provided with a weight scale so that the weight of the subject can be simultaneously measured when the subject stands on the determining device to measure the bioelectrical impedance Z through the feet for obtaining the body fat ratio FAT, function portions providing the weight scale may not be included in the visceral fat determining device 30. In this case, although the visceral fat determining device may not be able to measure the weight, it can measure the body fat ratio FAT from the measurement of the bioelectrical impedance Z through the feet and may perform the measurements associated with the visceral fat described above.

Furthermore, the body fat ratio measuring means may be configured to measure the bioelectrical impedance through the hands and feet of the subject and still perform the measurements described above as well. Specifically, the body fat ratio measuring means may be configured to measure the bioelectrical impedance between the hands of the subject as shown in FIGS. 1 and 5 and to measure the bioelectrical impedance Z between the feet of the subject as well as shown in FIG. 6.

Industrial Applicability

As has been described, according to the visceral fat determining device of the present invention, the abdominal visceral fat cross sectional area VA of the subject can be easily obtained at home. This offers an advantage that useful information on the visceral fat that is believed to be important with respect to various diseases can be easily obtained.

What is claimed is:

1. A visceral fat determining device comprising:
 input means for inputting personal data including an abdominal girth WL which is a circumferential length of a torso of a subject;
 data processing unit that stores the personal data and calculates quantitative information on abdominal visceral fat of the subject based on the personal data; and
 a display portion that displays the personal data and a result of the calculation performed by the data processing unit, wherein
 the quantitative information on the abdominal visceral fat of the subject is calculated based on the abdominal girth WL of the subject.

2. The visceral fat determining device according to claim 1, wherein the quantitative information on the abdominal visceral fat is an amount of the abdominal visceral fat.

3. The visceral fat determining device according to claim 1, further comprising:
 body fat ratio measuring means for measuring a bioelectrical impedance Z of the subject through electrodes in contact with end portions of the subject's body and for calculating a body fat ratio FAT of the subject based on the measured bioelectrical impedance and the inputted personal data or part of the data, wherein
 the body fat ratio FAT obtained by the body fat ratio measuring means is displayed on the display portion.

4. The visceral fat determining device according to claim 1, wherein the abdominal girth $W_L$ is a circumferential length of an abdomen at $4^{th}$ lumbar vertebrae of the subject.

5. The visceral fat determining device according to any one of claim 1, wherein size measuring means is provided for measuring the abdominal girth WL.

6. The visceral fat determining device according to claim 5, wherein the abdominal girth WL measured through the size measuring means is inputted into the data processing unit.

7. A visceral fat determining device comprising:
 input means for inputting personal data including an abdominal girth $W_L$ that is a circumferential length of a torso of a subject;
 a data processing unit that stores the personal data and calculates an estimated value of an abdominal visceral fat cross sectional area VA of the subject based on the personal data; and
 a display portion that displays the personal data and a value of the calculation performed by the data processing unit, wherein
 the data processing unit stores a first regression coefficient and a first regression constant of the abdominal girth $W_L$ which are obtained based on statistical analysis of correlation between actually measured values of the abdominal visceral fat cross sectional area VA obtained in abdominal tomography of human bodies of random samples and values of the abdominal girth $W_L$ of the human samples, wherein
 the estimated value of an abdominal visceral fat cross sectional area VA of the subject is obtained based on a value of the abdominal girth $W_L$, the first regression coefficient of the abdominal girth $W_L$ of human, and the first regression constant.

8. The visceral fat determining device according to claim 7, further comprising:
 body fat ratio measuring means for measuring a bioelectrical impedance Z of a subject through electrodes in contact with end portions of the subject's body and for obtaining a body fat ratio FAT of the subject based on the measured bioelectrical impedance Z and the inputted personal data or part of the data; and
 a display portion that displays a body fat ratio FAT measured with the body fat ratio measuring means.

9. The visceral fat determining device according to claim 7, wherein the calculation of an estimated value of the abdominal visceral fat cross sectional area VA of the subject is performed with addition of a correction term of the age and/or a correction term of the sex of the subject.

10. The visceral fat determining device according to claim 7, wherein an estimated value of the abdominal visceral fat cross sectional area VA of the subject is displayed on the display portion in accordance with a plurality of ranking levels which are pre-defined by a plurality of standard values of the abdominal visceral fat cross sectional area.

11. A visceral fat determining device comprising:
 input means for inputting personal data including an abdominal girth $W_L$ that is a circumferential length of a torso of a subject, height, and weight of the subject;
 a data processing unit that stores the personal data and calculates an estimated value of an abdominal visceral fat cross sectional area VA of the subject based on the personal data; and
 a display portion that displays the personal data and a result of the calculation performed by the data processing unit, wherein the data processing unit stores a second regression coefficient of the abdominal girth $W_L$, a first regression coefficient of BMI, and a second regression constant which are obtained based on statistical analysis of correlation between actually measured values of the abdominal visceral fat cross sectional area VA obtained in abdominal tomography of human bodies of random samples and values of the abdominal girth $W_L$ of the human samples and values of the BMI related to the level of the obesity of the human samples, and the estimated value of the abdominal visceral fat cross sectional area VA of the subject is obtained based on a value of the abdominal girth $W_L$, a value of the BMI, the second regression coefficient of the abdominal girth $W_L$, the first regression coefficient of the BMI, and the second regression constant.

12. A visceral fat determining device comprising:

input means for inputting personal data including an abdominal girth $W_L$ that is a circumferential length of a torso of a subject, height, weight, sex, and age of the subject;

a data processing unit that stores the personal data and calculates an estimated value of an abdominal visceral fat cross sectional area VA of the subject based on the personal data;

a display portion that displays the personal data and a result of the calculation performed by the data processing unit; and body fat ratio measuring means for measuring a bioelectrical impedance Z of the subject through electrodes in contact with end portions of the subject's body and for obtaining a body fat ratio FAT of the subject based on the measured bioelectrical impedance Z and the inputted personal data or part of the data, wherein the data processing unit stores a third regression coefficient of the abdominal girth $W_L$, a first regression coefficient of the body fat ratio FAT, and a third regression constant which are obtained based on statistical analysis of correlation between actually measured values of the abdominal visceral fat cross sectional area VA obtained in abdominal tomography of human bodies of random samples and values of the abdominal girth $W_L$ of the human samples and values of the body fat ratio FAT of the human samples, and the estimated value of the abdominal visceral fat cross sectional area VA of the subject is obtained based on a value of the abdominal girth $W_L$, a value of the body fat ratio FAT obtained with the body fat ratio measuring means, the third regression coefficient of the abdominal girth $W_L$, the first regression coefficient of the body fat ratio FAT, and the third regression constant.

13. The visceral fat determining device according to claim 12, wherein the calculation of an estimated value of the abdominal visceral fat cross sectional area VA of the subject is performed with addition of a correction term of the age and/or a correction term of the sex of the subject.

14. The visceral fat determining device according to claim 12, wherein an estimated value of the abdominal visceral fat cross sectional area VA of the subject is displayed on the display portion in accordance with a plurality of ranking levels which are pre-defined by a plurality of standard values of the abdominal visceral fat cross sectional area.

15. A visceral fat determining device comprising:

input means for inputting personal data including an abdominal girth $W_L$ that is a circumferential length of a torso of a subject, height, weight, and a thickness of abdominal subcutaneous fat s of the subject;

a data processing unit that stores the personal data and calculates an estimated value of an abdominal visceral fat cross sectional area VA of the subject based on the personal data; and a display portion that displays the personal data and a result of the calculation performed by the data processing unit, wherein the data processing unit stores a fourth regression coefficient of the abdominal girth $W_L$, a second regression coefficient of BMI, a first regression coefficient of the thickness of abdominal subcutaneous fat s, and a fourth regression constant which are obtained based on statistical analysis of correlation between actually measured values of the abdominal visceral fat cross sectional area VA obtained in abdominal tomography of human bodies of random samples and values of the BMI related to the level of the obesity of the human samples and values of the thickness of the abdominal subcutaneous fat s of the human samples, and the estimated value of the abdominal visceral fat cross sectional area VA of the subject is obtained based on a value of the abdominal girth $W_L$, a value of the BMI, a value of the thickness of abdominal subcutaneous fat s, the fourth regression coefficient of the abdominal girth $W_L$, the second regression coefficient of the BMI, the first regression coefficient of the thickness of abdominal subcutaneous fat s, and the fourth regression constant.

16. The visceral fat determining device according to claim 15, wherein an abdominal subcutaneous fat cross sectional area SA is further obtained based on the thickness of the abdominal subcutaneous fat s and the abdominal girth $W_L$ of the subject.

17. The visceral fat determining device according to claim 16, wherein a ratio of the estimated value of an abdominal visceral fat cross sectional area VA to the abdominal subcutaneous fat cross sectional area SA, VSR, is further obtained.

18. The visceral fat determining device according to claim 16, wherein a total abdominal fat cross sectional area WA is further obtained based on the estimated value of an abdominal visceral fat cross sectional area VA and the abdominal subcutaneous fat cross sectional area SA.

19. A visceral fat determining device comprising:

input means for inputting personal data including an abdominal girth $W_L$ that is a circumferential length of a torso of a subject, height, weight, sex, age, and a thickness of abdominal subcutaneous fat s of the subject;

a data processing unit that stores the personal data and calculates an estimated value of an abdominal visceral fat cross sectional area VA of the subject based on the personal data;

a display portion that displays the personal data and a result of the calculation performed by the data processing unit; and body fat ratio measuring means for measuring a bioelectrical impedance Z of the subject through electrodes in contact with end portions of the subject's body and for obtaining a body fat ratio FAT of the subject based on the measured bioelectrical impedance Z and the inputted personal data or part of the data, wherein the data processing unit stores a fifth regression coefficient of the abdominal girth $W_L$, a second regression coefficient of the body fat ratio FAT, a second regression coefficient of the thickness of abdominal subcutaneous fat s, and a fifth regression constant which are obtained based on statistical analysis of correlation between actually measured values of the abdominal visceral fat cross sectional area VA obtained in abdominal tomography of human bodies of random samples and values of the abdominal girth $W_L$ of the human samples, values of the body fat ratio FAT of the human samples, and values of the thickness of abdominal subcutaneous fat s, wherein the estimated value of an abdominal visceral fat cross sectional area VA of the subject is obtained based on a value of the abdominal girth $W_L$, a value of the body fat ratio FAT obtained with the body fat ratio measuring means, a value of the thickness of abdominal subcutaneous fat s, the fifth regression coefficient of the abdominal girth $W_L$, the second regression coefficient of the body fat ratio FAT, and the second regression coefficient of the thickness of abdominal subcutaneous fat s, and the fifth regression constant.

20. The visceral fat determining device according to claim 19, wherein an abdominal subcutaneous fat cross sectional area SA is further obtained based on the thickness of abdominal subcutaneous fat s and the abdominal girth $W_L$ of the subject.

21. The visceral fat determining device according to claim 20, wherein a ratio of the estimated value of an abdominal visceral fat cross sectional area VA to the abdominal subcutaneous fat cross sectional area SA, VSR, is further obtained.

22. The visceral fat determining device according to claim 20, wherein a total abdominal fat cross sectional area WA is further obtained based on the estimated value of the abdominal visceral fat cross sectional area VA and the abdominal subcutaneous fat cross sectional area SA.

23. A visceral fat determining device comprising:

input means for inputting personal data including an abdominal girth $W_L$ that is a circumferential length of a torso of a subject and height of the subject;

a data processing unit that stores the personal data and calculates an estimated value of an abdominal visceral fat cross sectional area VA of the subject based on the personal data; and a display portion that displays the personal data and a result of the calculation performed by the data processing unit, wherein the data processing unit stores a first regression coefficient of an abdominal girth index and a sixth regression constant which are obtained based on statistical analysis of correlation between actually measured values of the abdominal visceral fat cross sectional area VA obtained in abdominal tomography of human bodies of random samples and values of the abdominal girth index obtained based on the abdominal girth $W_L$ and height of the human samples, and the estimated value of an abdominal visceral fat cross sectional area VA of the subject is obtained based on a value of the abdominal girth index, the first regression coefficient of the abdominal girth index, and the sixth regression constant.

24. A visceral fat determining device comprising:

input means for inputting personal data including an abdominal girth $W_L$ that is a circumferential length of a torso of a subject and height of the subject;

a data processing unit that stores the personal data and calculates an estimated value of an abdominal visceral fat cross sectional area VA of the subject based on the personal data;

a display portion that displays the personal data and a result of the calculation performed by the data processing unit; and impedance measuring means for measuring a bioelectrical impedance Z of the subject through electrodes in contact with end portions of the subject's body, wherein the data processing unit stores an eighth regression coefficient of the abdominal girth $W_L$, a first regression coefficient of a term $(T_L^2/Z)$, and an eleventh regression constant which are obtained based on statistical analysis of correlation between the actually measured values of the abdominal visceral fat cross sectional area VA obtained in abdominal tomography of human bodies of random samples and values of the abdominal girth $W_L$ of the human samples and values of the term $(T_L^2/Z)$ obtained by dividing a square of a height $T_L^2$ by the bioelectrical impedance Z, and the estimated value of an abdominal visceral fat cross sectional area VA of the subject is obtained based on a value of the abdominal girth $W_L$, a value of the bioelectrical impedance Z measured with the impedance measuring means, a value of the height $T_L$ obtained through the input means, the eighth regression coefficient of the abdominal girth $W_L$, the first regression coefficient of the term $(T_L^2/Z)$, and the eleventh regression constant.

25. A visceral fat determining device comprising:

input means for inputting personal data including an abdominal girth $W_L$ that is a circumferential length of a torso of a subject and height of the subject;

a data processing unit that stores the personal data and calculates an estimated value of an abdominal visceral fat cross sectional area VA of the subject based on the personal data;

a display portion that displays the personal data and a result of the calculation performed by the data processing unit; and impedance measuring means for measuring a bioelectrical impedance Z of the subject through electrodes in contact with end portions of the subject's body, wherein the data processing unit stores a ninth regression coefficient of the abdominal girth $W_L$, a first regression coefficient of the bioelectrical impedance Z, and a twelfth regression constant which are obtained based on statistical analysis of correlation between the actually measured values of the abdominal visceral fat cross sectional area VA obtained in abdominal tomography of human bodies of random samples and values of the abdominal girth $W_L$ of the human samples and values of the bioelectrical impedance Z, and the estimated value of an abdominal visceral fat cross sectional area VA of the subject is obtained based on a value of the abdominal girth $W_L$, a value of the bioelectrical impedance Z measured with the impedance measuring means, the ninth regression coefficient of the abdominal girth $W_L$, the first regression coefficient of the bioelectrical impedance Z, and the twelfth regression constant.

26. A visceral fat determining device comprising:

input means for inputting personal data including an abdominal girth $W_L$ that is a circumferential length of a torso of a subject, height, weight, sex, and age of the subject;

a data processing unit that stores the personal data and calculates an estimated value of an abdominal visceral fat cross sectional area VA of the subject based on the personal data;

a display portion that displays the personal data and a result of the calculation performed by the data processing unit; and body fat ratio measuring means for measuring a bioelectrical impedance Z of the subject through electrodes in contact with end portions of the subject's body and for obtaining a body fat ratio FAT of the subject based on the measured bioelectrical impedance Z and the inputted personal data or part of the data, wherein the data processing unit stores a first regression coefficient of a term ($W_L^2 \cdot T_L \cdot age$), a first regression coefficient of a term ($W_L^2 \cdot T_L \cdot FAT$) and a thirteenth regression constant which are obtained based on statistical analysis of correlation between the actually measured values of the abdominal visceral fat cross sectional area VA obtained in abdominal tomography of human bodies of random male samples and values of the term ($W_L^2 \cdot T_L \cdot age$) obtained by multiplying a square of the abdominal girth $W_L^2$ of the human male samples, the height $T_L$ of the human male samples, and the age of the human male samples and values of the term ($W_L^2 \cdot T_L \cdot FAT$) obtained by multiplying a square of an abdominal girth $W_L^2$ of the human male samples, the height $T_L$ of the human male samples, and the body fat ratio FAT of the human male samples, and when inputted subject's personal data of sex is "male", the estimated value of an abdominal visceral fat cross sectional area VA of the subject is obtained based on a value of the abdominal girth $W_L$ of the subject, a value of the age of the subject inputted through the input means, a value of the body fat ratio FAT of the subject measured with the body fat ratio measuring means, the first regression coefficient of the term ($W_L^2 \cdot T_{L \cdot TL} \cdot age$), the first regression coefficient of the term ($W_L^2 \cdot T_L \cdot FAT$), and the thirteenth regression constant.

27. A visceral fat determining device comprising:

input means for inputting personal data including an abdominal girth $W_L$ that is a circumferential length of a torso of a subject, height, weight, sex, and age of the subject;

a data processing unit that stores the personal data and calculates an estimated value of an abdominal visceral fat cross sectional area VA of the subject based on the personal data;

a display portion that displays the personal data and a result of the calculation performed by the data processing unit; and body fat ratio measuring means for measuring a bioelectrical impedance Z of the subject through electrodes in contact with end portions of the subject's body and for obtaining a body fat ratio FAT of the subject based on the measured bioelectrical impedance Z and the inputted personal data or part of the data, wherein the data processing unit stores a second regression coefficient of the term ($W_L^2 \cdot T_L \cdot age$), a fifth regression coefficient of the body fat ratio FAT, and a fourteenth regression constant which are obtained based on statistical analysis of correlation between the actually measured values of the abdominal visceral fat cross sectional area VA obtained in abdominal tomography of human bodies of random female samples and values of the term ($W_L^2 \cdot T_L \cdot age$) obtained by multiplying a square of the abdominal girth $W_L^2$ of the human female samples, the height $T_L$ of the human female samples, and the age of the human female samples and values of the body fat ratio FAT of the human female samples, and when inputted subject's personal data of sex is "female", the data processing unit calculates the estimated value of an abdominal visceral fat cross sectional area VA of the female subject based on a value of the abdominal girth $W_L$ of the female subject, a value of the age of the female subject inputted through the input means, a value of the body fat ratio FAT of the female subject measured with the body fat ratio measuring means, the second regression coefficient of the term ($W_L^2 \cdot T_L \cdot age$), the fifth regression coefficient of the body fat ratio FAT, and the fourteenth regression constant.

* * * * *